United States Patent [19]
Camps et al.

[11] Patent Number: 5,423,876
[45] Date of Patent: Jun. 13, 1995

[54] INTRAMUSCULAR LEAD HAVING IMPROVED INSERTION

[75] Inventors: Antoine N. J. M. Camps, Eigs-Witten; Chrit W. Dreessen, Stein; Michael W. J. Polz, Kerkrade, all of Netherlands; Pierre A. Grandjean, Warsage, Belgium

[73] Assignee: Medtronic, Inc., Minneapolis, Minn.

[21] Appl. No.: 164,599

[22] Filed: Dec. 9, 1993

[51] Int. Cl.⁶ ................................. A61B 1/05
[52] U.S. Cl. ........................... 607/116; 607/132
[58] Field of Search .............. 607/119, 120, 37, 116, 607/9, 132, 72; 128/639, 642

[56] References Cited

U.S. PATENT DOCUMENTS

| | | | |
|---|---|---|---|
| 3,474,791 | 10/1969 | Bentov | 128/418 |
| 4,054,144 | 10/1977 | Hoffman et al. | 128/339 |
| 4,338,947 | 7/1982 | Williams | 128/642 |
| 4,341,226 | 7/1982 | Peters | 128/784 |
| 4,359,053 | 11/1982 | Benjamin | 128/339 |
| 4,411,268 | 10/1983 | Cox | 128/421 |
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,630,617 | 12/1986 | Ritter et al. | 128/784 |
| 4,711,251 | 12/1987 | Stokes | 128/784 |
| 4,735,205 | 4/1988 | Chachques et al. | 128/419 PG |
| 4,813,952 | 3/1989 | Khalafalla | 623/3 |
| 5,014,720 | 5/1991 | Barcel et al. | 128/786 |
| 5,086,787 | 2/1992 | Grandjean et al. | 128/786 |
| 5,324,323 | 6/1994 | Bui | 607/119 |
| 5,324,325 | 6/1994 | Moaddeb | 607/120 |

Primary Examiner—Lee S. Cohen
Assistant Examiner—Brian M. Green
Attorney, Agent, or Firm—Michael J. Jaro; Harold R. Patton

[57] ABSTRACT

An intramuscular lead for the electrical stimulation of muscle tissue. The improved lead has a needle connected to a strand of suture, a coiled conductor coupled to the strand by a tapered section of the coiled conductor, an insulative cover covers part of the coiled conductor, and a terminal connector coupled to the coiled conductor provides a connection to a pulse generator. Through such a construction the lead may be more readily introduced through muscle tissue.

20 Claims, 4 Drawing Sheets

INTRAMUSCULAR LEAD HAVING IMPROVED INSERTION

FIELD OF THE INVENTION

The present invention generally relates to skeletal muscle stimulation, and more particularly, it relates to an intramuscular lead system having an improved electrode end for easier insertion.

BACKGROUND OF THE INVENTION

Skeletal muscle tissue is often used to provide cardiac assistance. Such systems which utilize skeletal muscle tissue may be seen in U.S. Pat. No. 4,411,268, issued to Cox, and U.S. Pat. No. 4,813,952, issued to A. Khalafalla, and U.S. Pat. No. 4,735,205 all assigned to Medtronic, Inc., and incorporated herein by reference.

Such systems use a patient's own muscle tissue in conjunction with a implantable pulse generator to provide cardiac assistance. In comparison to presently available cardiac assist systems using wholly artificial structures, systems using a patient's skeletal muscle are extremely compact and energy efficient. Such cardiac assist systems, however, are not without limitations. One problem presented by the use of skeletal muscle power for cardiac assistance is the application of electrical stimulation signals to cause skeletal muscle contraction.

The electrical connection between an implantable pulse generator and the desired skeletal muscle is accomplished through a lead. Generally speaking a lead is a wire insulated along its length and having an electrode at one end and connectable to a pulse generator at its other end. Through a lead then electrical signal may be communicated to and from skeletal muscle tissue.

The earliest skeletal muscle powered cardiac assist systems used screw-in type leads for skeletal muscle stimulation. A major improvement to these leads is found in the use of steroid eluting pacing leads. U.S. Pat. No. 4,711,251 issued to Stokes, and assigned to Medtronic, Inc. teaches the use of an endocardial pacing lead having steroid drug embedded in the distal tip. This embedded steroid drug treats the heart tissue immediately in contact with the pacing electrode. U.S. Pat. Nos. 4,506,680; 4,577,642; and 4,606,118 teach similar endocardial leads, all of which treat the electrode contact area with asteroid. United States Statutory Invention Registration No. H356 discloses an endocardial pacing lead suitable for epicardial insertion which elutes a steroid drug from the electrode.

A further improvement in intramuscular lead technology arose with the adaptation of heart wire technology for chronic pacing use. Typically such leads are constructed as follows: A connector assembly has a coiled connector attached thereto. The coiled connector is insulated along a part of its length while a suture runs throughout its inner lumen, from the connector assembly to an end. At the end of the suture a helical portion is formed, and a needle is attached to the end of the suture. The suture material is treated with asteroid drug, such as a glucocorticosteroid, along its entire length. Additional drugs which may be imbedded within strand include antibiotics. Upon chronic implantation, the steroid drug is eluted from the suture material, thus treating possible tissue inflammation or damage caused by the implantation procedure or subsequent irritation.

One drawback to such a lead as presently configured is found at the conductor coil-suture interface. In designs presently in use the conductor coils are attached to the end of suture by a crimp sleeve. In such a manner a tip electrode is formed. Because the suture is used to pull the electrode coil through muscle tissue during implantation, crimp sleeve used to form tip electrode, which has a larger diameter than either suture or electrode coil, creates friction. Such friction creates difficulties to the physician during implantation. For this reason a flexible, specifically designed lead having a relatively slender dimension at the conductor coil-suture interface is desired.

SUMMARY OF THE INVENTION

Briefly, the above and further objects and features of the present invention are realized by providing a new and improved intramuscular lead. The lead can be used to electrically stimulate muscle tissue that are configured for a cardiac assist system powered by surgically modified skeletal muscle tissue. The skeletal muscle is either wrapped about the heart itself, or about an auxiliary pumping chamber attached to the aorta. Electrical stimulation is supplied via the intramuscular lead to cause contraction of the skeletal muscle in synchrony with the natural or artificially paced heart rate and timed to obtain the desired hemodynamic effect. The improved lead has an electrode which is embedded in the skeletal muscle. The electrode is attached to a suture through a tapered section of electrode coil. Through such a taper the electrode coil and suture are firmly joined.

BRIEF DESCRIPTION OF THE DRAWINGS

The above and other options, features and advantages of the present invention will be more apparent from the following more particular description thereof, presented in conjunction with accompanying drawings, wherein.

DETAILED DESCRIPTION OF THE PREFERRED EMBODIMENT

Cardiac assist systems utilizing electrically stimulated skeletal muscle supplement the heart in performing blood circulation. This assistance may take two basic forms. The first of these directly assist the natural heart by increasing aortic pressure at the same time as the heart. This may be implemented by wrapping the skeletal muscle about the heart. The second form increases circulatory system pressure during relaxation of the heart. The resulting increase in coronary perfusion provides the desired assistance to the heart by increasing myocardial oxygen supply.

With either form of cardiac assist, the heart is electrically sensed to ensure that the skeletal muscle is stimulated in the proper timing relationship to heart contractions.

Figure 1:
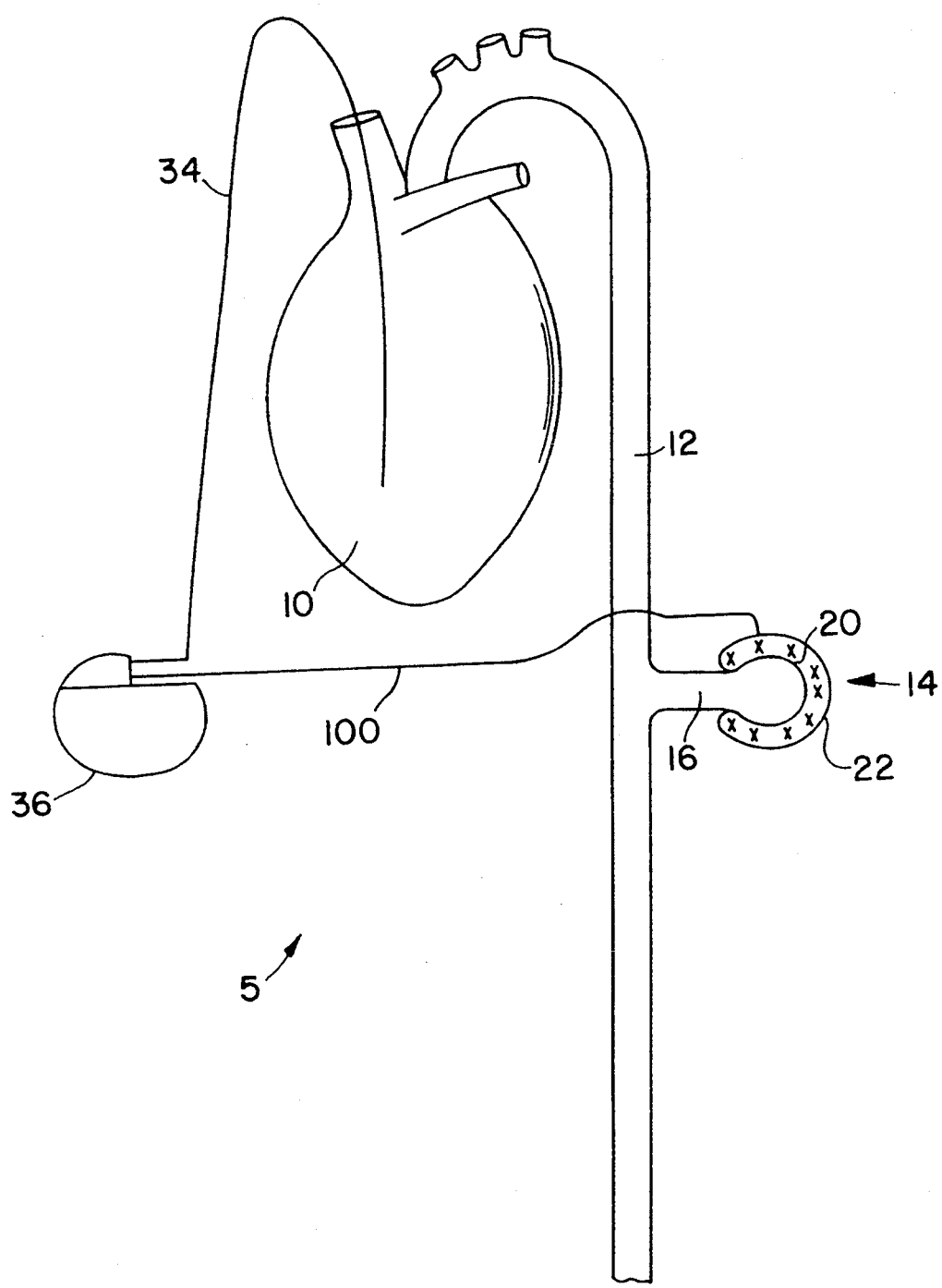
FIG. 1 is an schematic view of one configuration of a cardiac assist system.

FIG. 1 shows a typical cardiac assist system 5 used to provide indirect assistance to the cardiac function. Specifically this particular mode performs counter pulsation for enhanced perfusion. As discussed above, enhanced perfusion increased myocardial oxygen supply. It should be understood that this particular mode of cardiac assist is shown for the purpose of illustration only and not by way of limiting the scope of the present invention. Other modes of cardiac assist may be found in U.S. Pat. No. 4,813,952.

The human heart 10 is assisted by counterpulse contraction of skeletal muscle 22 and this results in the enhanced perfusion of cardiac tissue. Pulse generator 36 senses contractions of human heart 10 by lead 34. After a delay, pulse generator 36 sends stimulating pulses to skeletal muscle 22 via lead 100, thereby inducing contraction. As skeletal muscle 22 contracts, it reduces the diameter of chamber 20 which is coupled to aorta 12 via stub 16. This contraction increases aortic pressure, thereby improving perfusion through the coronary vascular system.

Skeletal muscle 22 must be conditioned to respond in the desired manner without or at least with minimal fatigue. U.S. Pat. No. 4,411,268 issued to James Cox, incorporated herein by reference, teaches such a method of conditioning.

Figure 2:
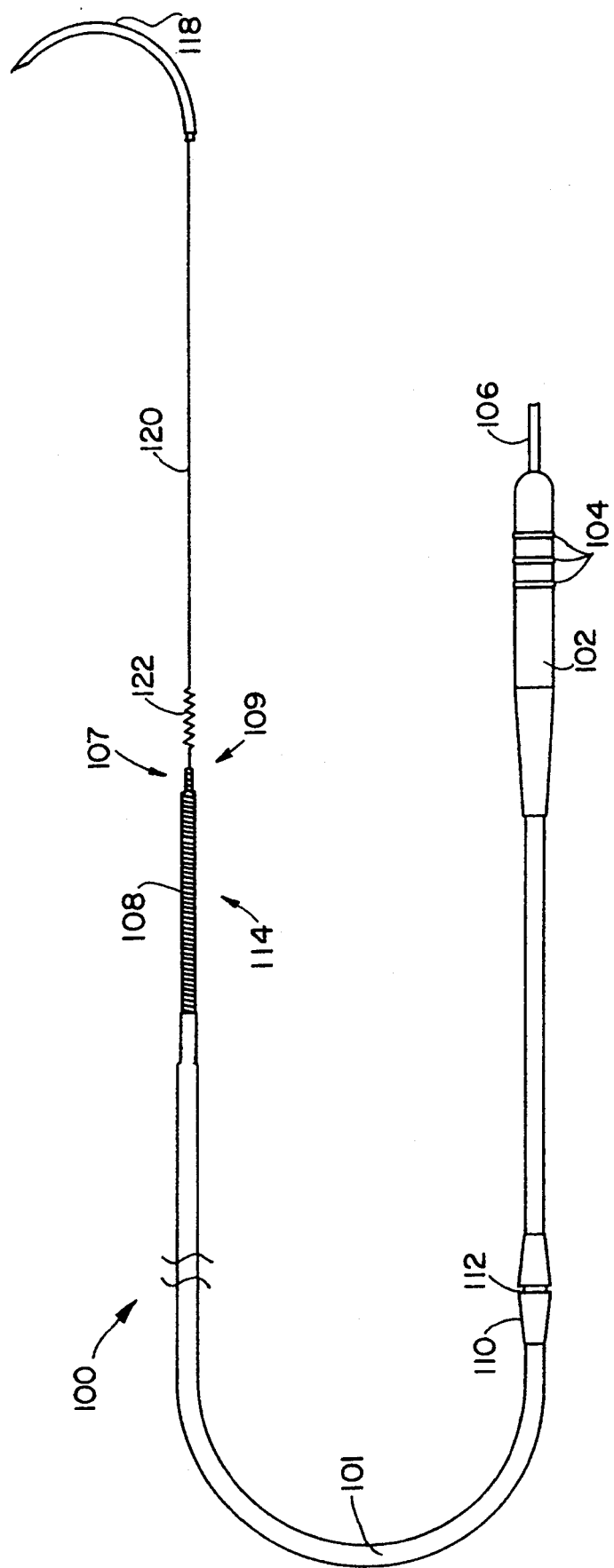
FIG. 2 is a plan view of a chronically implantable stimulation lead according to the present invention.

FIG. 2 is a plan view of a chronically implantable lead 100 according to the present invention for stimulation of skeletal muscle 22 which powers cardiac assist system 5 of FIG. 1. Proximal end of lead 34 contains a connector 102 which couples to pulse generator 36 (not shown in FIG. 2.) A connector 102 has sealing rings 104 which provide a fluid tight connection with pulse generator 36. A terminal pin 106 electrically couples lead 100 to pulse generator 36.

An insulating sheath 101 electrically insulates lead 100, and specifically coiled conductor 108. Coiled conductor 108 is coupled at one end to connector 102 and runs to its distal end 107. An electrode 114 is fashioned from an uninsulated portion of coiled conductor 108. Electrode 114, therefor, may be electrically connected to pulse generator 36.

A strand 120 of suture material of polypropylene or other polymer is attached to distal end 107 of coiled conductor 108. A curved surgical needle 118 is mechanically attached to distal end of strand 120 of suture material.

A drug (such as a steroid or antibiotic) may be releasably imbedded within the polymer of strand 120. During the life of lead 100, this drug elutes out into the surrounding tissue at a predetermined rate. Preformed helix 122 is deformably molded into strand 120. Further description of imbedding a drug within strand 120 may be found in U.S. Pat. No. 5,086,787 to Grandjean et al., incorporated herein by reference. A detailed explanation of preformed helix 122 is found in U.S. Pat. No. 4,341,226 issued to Peters, incorporated herein by reference.

Figure 3:
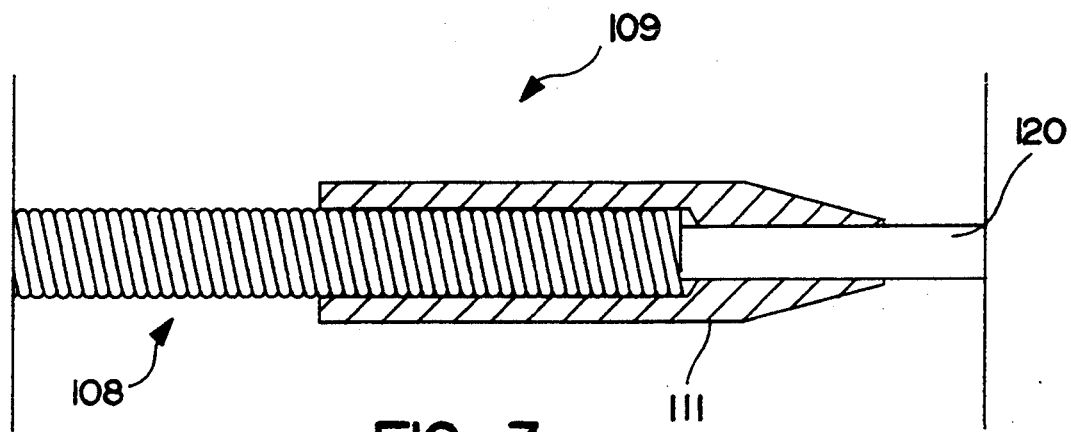
FIG. 3 is an enlarged partial view of the coiled conductor-suture interface of chronically implantable stimulation lead according to the prior art.

FIG. 3 is an enlarged partial view of coiled conductor-suture interface 109 of a stimulation lead 34 according to the prior art. As seen coiled conductor 108 was attached to strand 120 through a crimp core 111. As seen crimp core 111 presents a relatively bulky dimension, and specifically wider diameter, as compared to coiled conductor 108 and strand 120.

Figure 4:
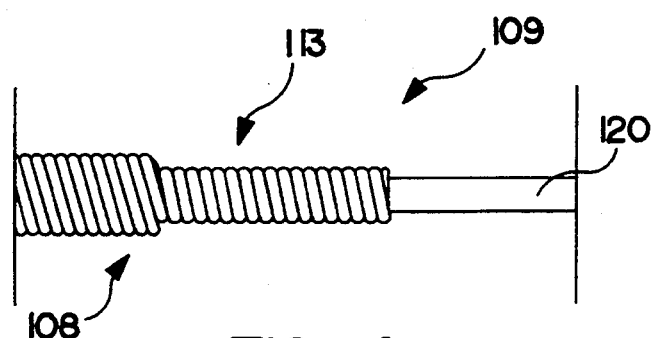
FIG. 4 is an enlarged partial view of the coiled conductor-suture interface of a chronically implantable stimulation lead according to the present invention.

FIG. 4 is an enlarged partial view of coiled conductor-suture interface 109 of a stimulation lead 34 according to the present invention. As seen coiled conductor 108 is attached to strand 120 through use of a taper 113. Specifically coiled conductor 108 is tapered to a dimension so that it firmly is attached to strand 120. Taper 113 may be accomplished in any known manner including swaging. Although not specifically depicted the region of strand 120 engaged by taper 113 may be roughened so as to decrease its smoothness and enhance the grip of taper 113 thereto. Any suitable techniques may be used to provide such a rough surface including knurling strand 120. In addition an adhesive may also be applied to strand 120 in the vicinity of taper 113 to enhance the grip of taper 113 thereto. Finally to enhance the grip of taper 113 to strand 120 the coils of taper 113 may also be spot welded to one another once the strand and coiled are joined.

Figure 5:
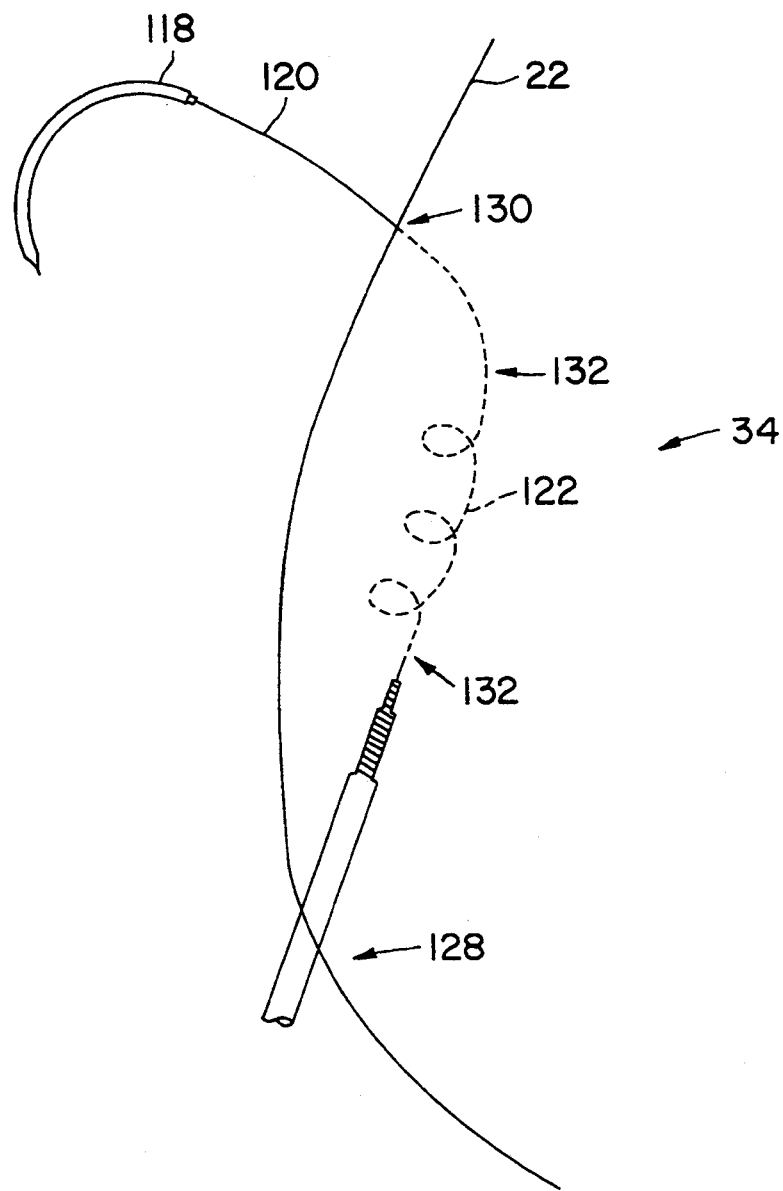
FIG. 5 is a schematic view of the chronically implantable lead according to the present invention positioned in a skeletal muscle.

FIG. 5 is a schematic view of lead 34 according to the present invention positioned in a skeletal muscle. As seen needle 118 enters skeletal muscle 22 at puncture 128. It proceeds along path 132 and exits skeletal muscle 22 at exit point 130. As needle 118 proceeds through muscle 22 it pulls strand 120 and coiled conductor 108 therewith. Because taper 113 is dimensioned as less than the widest dimension of coiled conductor 108 lead 34 may be inserted relatively easier than the lead featuring interface 109 shown in FIG. 3. Preformed helix 122 sustains electrode 114 in contact with skeletal muscle 22 at puncture point 128. If glucocorticosteroid is used, it elutes out from strand 120 all along path 132 including puncture 128 and exit point 130 to minimize acute and chronic inflammation.

Figure 6:
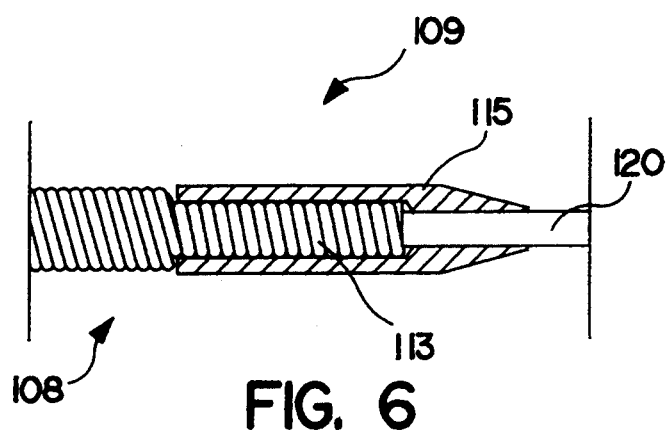
FIG. 6 is an enlarged partial view of the coiled conductor-suture interface of an alternate embodiment for a chronically implantable stimulation lead according to the present invention.

FIG. 6 is an enlarged partial view of coiled conductor-suture interface 109 of an alternate embodiment for a chronically implantable stimulation lead according to the present invention. This embodiment is the same as that previously described with the exception of a retaining collar 115 positioned on taper 113. Collar 115 is stressed to provide additional clamping to strand 120 from coiled conductor 108. As seen collar 115 presents dimension no larger than coiled conductor 108.

While the embodiment of the present invention has been described in particular application to cardiac assist technology, it will be understood the invention may be practiced in other electrode technologies where the aforementioned characteristics are desirable, including neurological and muscle stimulation applications.

Furthermore, although the invention has been described in detail with particular reference to a preferred embodiment, it will be understood variations and modifications can be effected within the scope of the following claims. Such modifications may include substituting elements or components which perform substantially the same function in substantially the same way to achieve substantially the same result for those described herein.

What is claimed is:

1. An implantable lead for stimulation of a skeletal muscle comprising:
   a needle;
   a strand of suture connected to said needle;
   a coiled conductor having a tapered section, said tapered section being coupled to said strand said coiled conductor;

an insulative cover over part of said coiled conductor; and terminal connector means coupled to said coiled conductor to provide a connection to a pulse generator.

2. The lead according to claim 1, further comprising a collar about said tapered section.

3. The lead according to claim 2, wherein said strand is treated with an elutable drug.

4. The lead according to claim 3, wherein said drug is a glucocorticosteroid.

5. The lead according to claim 3 wherein said drug is an antibiotic.

6. An implantable lead for stimulation of a skeletal muscle comprising:

a curved needle;

a strand of suture, said strand having a first section and a second section, said second section being connected to said needle;

a coiled conductor having a first section and a second section, said second section of said coiled conductor being tapered, said second section of said coiled conductor further coupled to said first section of said strand;

an insulative cover over part of said coiled conductor; and terminal connector means coupled to said coiled conductor to provide a connection to a pulse generator.

7. The lead according to claim 6 wherein said first section of said strand being smooth.

8. The lead according to claim 6 wherein said first section of said strand being knurled.

9. The lead according to claim 6 further comprising an adhesive on said first section of said strand.

10. The lead according to claim 6, wherein said strand is treated with an elutable drug.

11. The lead according to claim 10, wherein said drug is a glucocorticosteroid.

12. The lead according to claim 10 wherein said drug is an antibiotic.

13. The lead according to claim 6 further comprising a collar about said second section of said coiled conductor.

14. A system for stimulation of body tissue comprising:

a needle;

a strand of suture, said strand having a first section and a second section, said second section connected to said needle;

a coiled conductor having a first section and a second tapered section, the coiled conductor connected to said strand by said second tapered section;

an insulative cover over said first section of said coiled conductor;

terminal connector means coupled to said coiled conductor to provide a connection;

and a pulse generator connected to said terminal connector means, said pulse generator emitting electrical stimulation signals.

15. The lead according to claim 14 wherein said first section of said strand being smooth.

16. The lead according to claim 14 wherein said first section of said strand being knurled.

17. The lead according to claim 14 further comprising an adhesive on said first section of said strand.

18. The lead according to claim 14 wherein said strand is treated with elutable drug.

19. The lead according to claim 18, wherein said drug is a glucocorticosteroid.

20. The lead according to claim 14 further comprising a collar about said second section of said coiled conductor.

* * * * *